(12) United States Patent
Gong et al.

(10) Patent No.: US 10,106,751 B2
(45) Date of Patent: Oct. 23, 2018

(54) RAPID ESTIMATION OF FEED POTENTIAL FOR BASE OIL FORMATION

(71) Applicant: ExxonMobil Research and Engineering Company, Annandale, NJ (US)

(72) Inventors: Liezhong Gong, Basking Ridge, NJ (US); Corry S. Powers, Spring, TX (US); Eric D. Joseck, Spring, TX (US); Beatrice M. Gooding, Hopewell, NJ (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 31 days.

(21) Appl. No.: 15/368,888

(22) Filed: Dec. 5, 2016

(65) Prior Publication Data

US 2017/0166827 A1    Jun. 15, 2017

Related U.S. Application Data

(60) Provisional application No. 62/265,592, filed on Dec. 10, 2015.

(51) Int. Cl.
   *C10G 73/02* (2006.01)
   *C10G 73/42* (2006.01)
   (Continued)

(52) U.S. Cl.
   CPC .............. *C10G 73/02* (2013.01); *C10G 21/00* (2013.01); *C10G 45/00* (2013.01); *C10G 45/02* (2013.01);
   (Continued)

(58) Field of Classification Search
   CPC ......... C10G 73/02; C10G 73/06–73/12; C10G 73/42–73/44; C10G 45/58;
   (Continued)

(56) References Cited

U.S. PATENT DOCUMENTS

| 5,419,185 A | 5/1995 | Chimenti et al. |
| 5,699,270 A | 12/1997 | Ashe et al. |

(Continued)

FOREIGN PATENT DOCUMENTS

GB    1304073 A    1/1973

OTHER PUBLICATIONS

Sharma, Brajendra K. et al., "Effects of hydroprocessing on structure and properties of base oils using NMR", Fuel Processing Technology, 2008, vol. 89. Issue 10, pp. 934-991.

(Continued)

*Primary Examiner* — Renee Robinson
(74) *Attorney, Agent, or Firm* — Scott F. Yarnell; Robert A. Migliorini

(57) ABSTRACT

Methods are provided for rapidly characterizing a feedstock being considered for lubricant base oil production in order to determine the viscosity index potential of the feedstock. It has unexpectedly been discovered that the DDVI value for a feedstock at a specified pour point can be predicted based on a) the feed distillate residual wax content at a temperature as determined by Differential Scanning Calorimetry, such as the feed distillate residual wax content at a temperature corresponding to the specified pour point temperature; b) the feed distillate refractive index; c) the feed distillate kinematic viscosity at a temperature, such as kinematic viscosity at 100° C.; and d) the distillate volume-averaged boiling point. Based on this unexpected correlation, the VI potential of a feedstock can be determined based on measurement of (Continued)

properties that can be performed on a time scale corresponding to one or a few days using a few milliliters of feedstock.

16 Claims, 6 Drawing Sheets

(51) Int. Cl.
| | |
|---|---|
| *G01N 33/28* | (2006.01) |
| *G01N 33/30* | (2006.01) |
| *C10M 101/02* | (2006.01) |
| *C10G 21/00* | (2006.01) |
| *C10G 45/58* | (2006.01) |
| *C10G 45/02* | (2006.01) |
| *C10G 45/00* | (2006.01) |
| *G01N 25/48* | (2006.01) |
| *C10M 169/00* | (2006.01) |

(52) U.S. Cl.
CPC ............ *C10G 45/58* (2013.01); *C10G 73/42* (2013.01); *C10M 101/02* (2013.01); *C10M 169/00* (2013.01); *G01N 25/4866* (2013.01); *G01N 33/2811* (2013.01); *G01N 33/2823* (2013.01); *G01N 33/2888* (2013.01); *G01N 33/30* (2013.01); *C10G 2300/30* (2013.01)

(58) Field of Classification Search
CPC .............. G01N 25/4866; G01N 33/28; G01N 33/2811; G01N 33/2823; G01N 33/2888; G01N 33/30
See application file for complete search history.

(56) References Cited

U.S. PATENT DOCUMENTS

| | | |
|---|---|---|
| 6,295,485 B1 | 9/2001 | Gleeson et al. |
| 6,317,654 B1 | 11/2001 | Gleeson et al. |
| 7,875,458 B2 | 1/2011 | Eagan et al. |
| 8,992,770 B2 | 3/2015 | Gong et al. |
| 2010/0070202 A1 | 3/2010 | Gould et al. |
| 2013/0021607 A1 | 1/2013 | Kanvinde et al. |

OTHER PUBLICATIONS

Verdier, Sylvain et al., "A critical approach to viscosity index", Fuel, 2009, vol. 88, pp. 2199-2206.
The International Search Report and Written Opinion of PCT/US2016/064922 dated Feb. 28, 2017.

RAPID ESTIMATION OF FEED POTENTIAL FOR BASE OIL FORMATION

CROSS-REFERENCE TO RELATED APPLICATIONS

This application claims priority to U.S. Provisional Application Ser. No. 62/265,592 filed Dec. 10, 2015, which is herein incorporated by reference in its entirety.

FIELD

This description is related to characterization of feeds for use in formation of lubricating base oils.

BACKGROUND

Composition-based tools provide the ability to screen potential whole crude oils or partial crude fractions for plant test runs and subsequent base oil quality evaluations by providing predictions of the potential product qualities and/or yields that may be expected from a feedstock. Composition-based tools typically require detailed compositional characterization of a potential feedstock to ensure proper prediction accuracy.

A possible use of composition-based tools for prediction of product properties is in analysis of potential feeds for lubricant base oil production. Unfortunately, the ability to predict product yields and/or properties using currently available composition-based tools is limited. For example, viscosity index (VI) is an important product quality for determining the value and/or usage of a lubricant product. Current composition-based models, however, are unable to consistently provide accurate predictions of the potential VI values for lubricant base oils that can be made from a feedstock. Because conventional composition-based models are not reliable, analysis of a crude oil feedstock (or a feedstock containing a mixture of crudes) to determine suitability for lubricant base oil production is currently based on performing a full assay of the feed. Performing an assay for lube production potential can require a sample size on the order of hundreds of liters and can further require several months of time. It would be desirable to have a method for determining potential VI values for lubricant based oils produced from a feedstock that can be performed on a significantly shorter time scale.

U.S. Pat. No. 6,317,654 describes use of composition-based models for prediction of properties for finished lube products formed from a feed. After performing a characterization of a potential feed, the characterized potential feed can be compared with other feeds in the composition based model to identify similar feeds. Predictions of base oil properties for the potential feed can then be made based on compositional model. The predicted properties include thermal and oxidation stability of finished products formulated from base oils derived from processing of a feed.

U.S. Pat. No. 8,992,770 describes a method for characterizing crude oils as potential feedstocks for production of lubricant base oils. A potential feedstock can be characterized based on isoparaffin content and dewaxed distillate viscosity index to determine the suitability for use in lubricant base oil production. Feedstocks with a dewaxed distillate viscosity index at a pour point of −9° C. of less than 0 are described as being less favorable for use in lubricant base oil production.

U.S. Patent Application Publication 2010/0070202 describes a method for predicting low temperature properties of a formulated lubricant oil based on characterization of the corresponding base oil. The low temperature properties are predicted based on characterization of the base oil using Differential Scanning Calorimetry (DSC).

SUMMARY

In an aspect, a method for determining feedstock quality for lubricant base oil production is provided, the method comprising: determining a wax content of a distillate feedstock fraction by differential scanning calorimetry; obtaining a characteristic boiling point, a characteristic viscosity, and a refractive index for the distillate feedstock fraction; calculating a distillate dewaxed viscosity index (DDVI) at a DDVI-temperature for the distillate feedstock fraction based on the determined wax content and at least two of the obtained characteristic boiling point, the obtained characteristic viscosity, and the obtained refractive index, the calculated DDVI being at least 0 at the DDVI-temperature; and processing the feedstock to form a lubricant base oil having a viscosity index of at least 80 and a pour point of 0° C. or less.

In another aspect, a method for determining feedstock quality for lubricant base oil production is provided, the method comprising: determining a wax content of a distillate feedstock fraction by differential scanning calorimetry; measuring at least two of a characteristic boiling point, a characteristic viscosity, and a refractive index for the distillate feedstock fraction; calculating a distillate dewaxed viscosity index (DDVI) at −9° C. for the distillate feedstock fraction based on the determined wax content and the measured at least two of the characteristic boiling point, the characteristic viscosity, and the refractive index, the calculated DDVI being at least 0 at −9° C.; and processing the feedstock to form a lubricant base oil having a viscosity index of at least 80 and a pour point of 0° C. or less.

DETAILED DESCRIPTION

Figure 1:
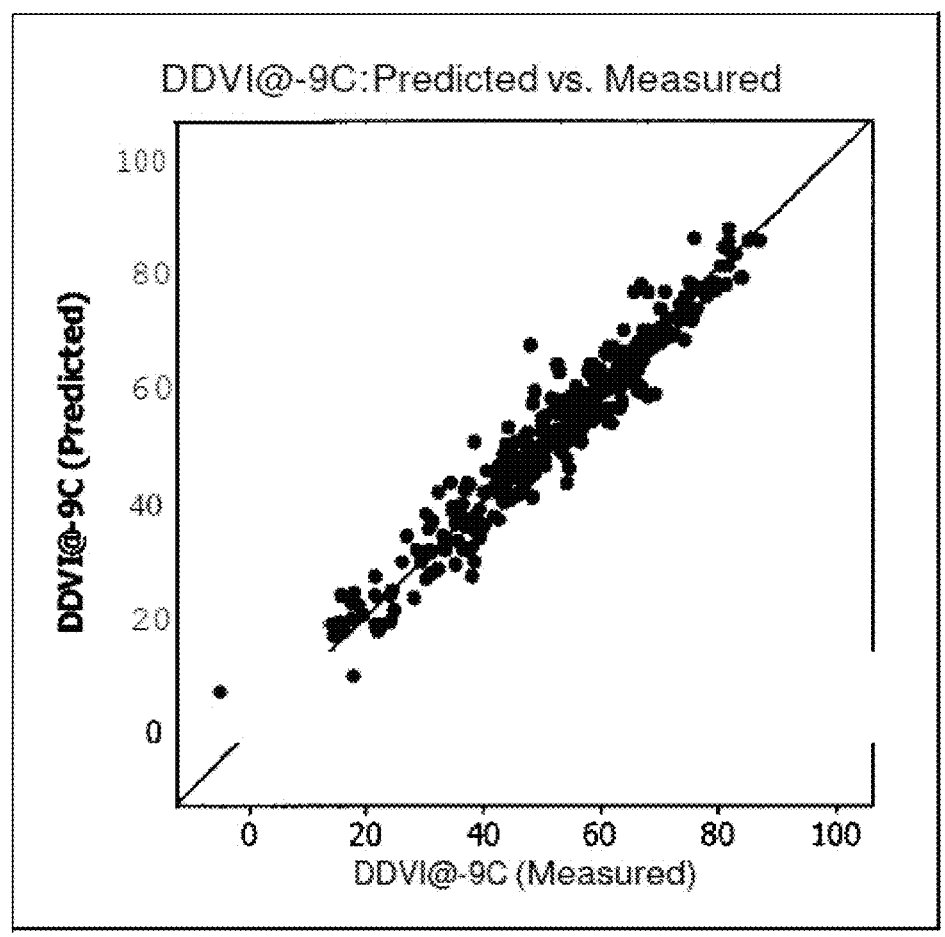
FIG. 1 shows an example of a correlation between DDVI values predicted using a model based on DSC wax content and measured DDVI values.

All numerical values within the detailed description and the claims herein are modified by "about" or "approximately" the indicated value, and take into account experimental error and variations that would be expected by a person having ordinary skill in the art.

Overview

In various aspects, systems and methods are provided for rapidly characterizing a feedstock being considered for lubricant base oil production in order to determine the viscosity index potential of the feedstock. It has unexpectedly been discovered that the DDVI value for a feedstock at a specified pour point can be predicted based on a) the feed distillate residual wax content at a temperature as determined by Differential Scanning Calorimetry, such as the feed distillate residual wax content at a temperature corresponding to the specified pour point temperature; b) the feed distillate refractive index; c) the feed distillate kinematic viscosity at a temperature, such as kinematic viscosity at 100° C.; and d) the distillate volume-averaged boiling point. Based on this unexpected correlation, the VI potential of a feedstock can be determined based on measurement of properties that can be performed on a time scale corresponding to one or a few days using a few milliliters of feedstock. The measurement tools needed for determining each of these quantities also correspond to tools that are suitable for use in a refinery setting. This is in contrast to performing a full assay, which could require multiple months and on the order of hundreds of liters of feedstock. This is also in contrast to performing solvent dewaxing on a feed to directly determine a DDVI value, which can require a dewaxing apparatus and several hundred milliliters of feedstock.

In a lube refining and/or converting processes for formation of lubricant base oils, the base oil viscosity index (VI) is typically used as a desired process target. For example, during solvent processing of a feed to produce Group I base oils, once the feed distillate and the process equipment hardware are determined, process conditions such as solvent/feed treat ratio, dewaxing tower bottom temperature, temperature gradient, and solvent(s) water content are adjusted to ensure the base oils meet the desired VI target(s). For a lubricant base oil production process that includes hydroprocessing, the conversion in the hydroprocessing unit (such as the 700° F.+ conversion) can also be adjusted to achieve a target base oil VI.

One of the difficulties in selecting a crude slate for a refinery is determining whether a potential crude slate will provide a suitable distillate fraction for lubricant base oil formation. As noted above, conventional techniques for accurately determining the VI potential of a feedstock can require performing a full assay on the crude oils within the feedstock. This can require testing with a time scale on the order of months. During this time, the crude oil (or crude oils) being considered for use in the crude slate either have to be stored or the refinery can risk processing the crude slate without knowing in advance whether base oils having desired combinations of viscosity and viscosity index can be produced.

Figure 4:
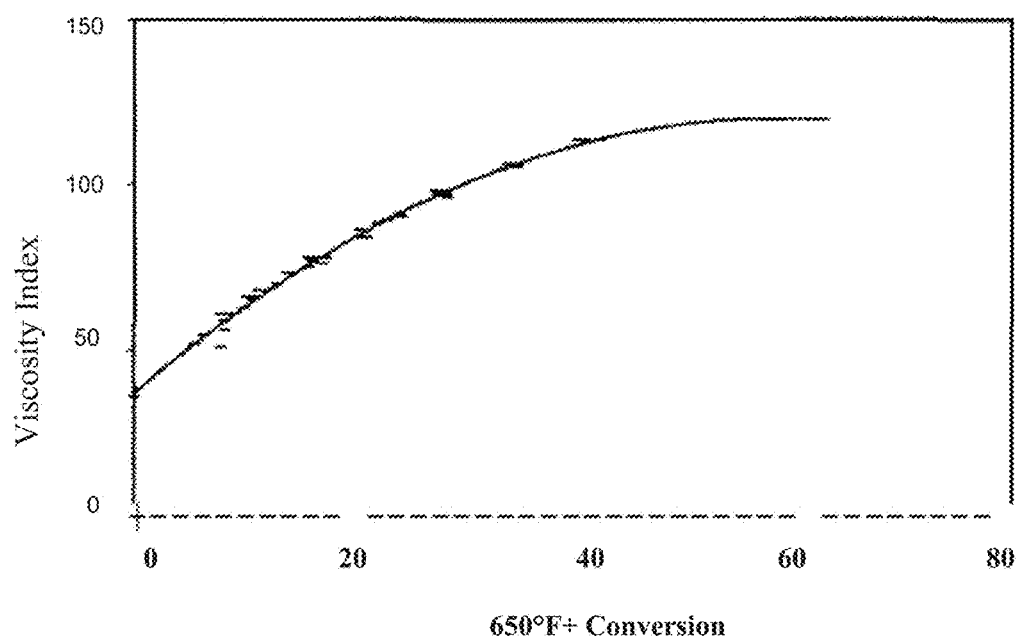
FIG. 4 shows a correlation between feedstock DDVI values and hydroprocessing severity for forming a lubricant base oil with a target VI value.

FIG. 4 shows an example of the change in VI for a base oil as the hydroprocessing severity for hydroprocessing of a feedstock is increased. Although FIG. 4 shows an example of using a feedstock that is suitable for production of lubricant base oils, the general features of FIG. 4 illustrate one of the potential problems of attempting to produce lubricant base oils from a feed without prior characterization of the VI potential. In the example shown in FIG. 4, the VI of a base oil produced by solvent dewaxing to a pour point of −9° C., without any hydroprocessing and/or aromatics extraction being performed, is about 50. This corresponds to the dewaxed distillate viscosity index (DDVI) at a pour point of −9° C. of the feedstock. When hydroprocessing is performed on the feed prior to dewaxing, FIG. 4 shows that increasing the severity of hydroprocessing of the feedstock can improve the VI at the target pour point, but this improvement levels off as the 700° F.+ conversion during hydroprocessing increases to more than 50%.

As illustrated in FIG. 4, increasing the severity of hydroprocessing can improve the VI of a resulting base oil. However, if the DDVI value is too low for a feedstock, such as a DDVI value at −9° C. pour point of 0 or less, the amount of VI uplift that can be achieved by hydroprocessing may not be sufficient to allow for production of base oils with a VI of at least 80 (i.e., Group I base oils). More generally, if the distillate portion of a feedstock does not have a proper lube VI potential, then the resulting base oils generated from the feed might not able to meet a desired VI target even using the most severe extraction seventies allowed by the process units (e.g., maximum treat ratio, and/or the highest tower temperature, etc.). This can result in the distillate portion of a feedstock being down-graded into lower value fuel stocks (e.g. FCC feedstocks).

Based on the unexpected discovery that the DDVI value for the distillate portion of a feed can be predicted based on a limited set of readily measured properties, a method is provided herein for rapid determination of the VI potential of a feedstock for lubricant base oil formation.

In this discussion, the "distillate" portion of a feed is defined as a portion of a feedstock that has a T5 distillation point of at least 650° F. and a T95 distillation point of 1100° F. or less. Such a portion can be created, for example, by separating a crude oil to form an atmospheric resid, followed by performing a vacuum distillation on the atmospheric resid to separate the "distillate" portion from a vacuum resid portion. Thus, the "distillate" portion of a feed corresponds to a portion that would normally be considered for use by one of skill in the art for formation of lubricant base oils. A T5 distillation point or boiling point refers to the temperature where 5 wt % of a feed will boil, while a T95 distillation point or boiling point refers to a temperature where 95 wt % of a feed will boil.

In this discussion, the "VI potential" of a feedstock refers to the ability of a feedstock to be solvent processed and/or hydroprocessed to make a commercially suitable base oil, such as a Group I base oil. The definition for VI potential can be dependent on the desired VI and desired pour point for a base oil. Examples of desired or target VI values can be a VI value of at least 80, or at least 85, or at least 90, or at least 95, or at least 100, or at least 105, and/or up to about 130 or less, or about 120 or less. Examples of desired or target pour points for a base oil having a desired or target VI value can be a pour point of 0° C. or less, or −6° C. or less, or −9° C. or less, or −12° C. or less, or −15° C. or less, and optionally as low as a pour point of at least −45° C., or possibly still lower. A feedstock having a suitable VI potential can correspond to a feedstock having a predicted DDVI value of at least about 0, or at least about 10, or at least about 20.

Group I basestocks or base oils are defined as base oils with less than 90 wt % saturated molecules and/or at least 0.03 wt % sulfur content. Group I basestocks also have a viscosity index (VI) of at least 80 but less than 120. Group II basestocks or base oils contain at least 90 wt % saturated molecules and less than 0.03 wt % sulfur. Group II basestocks also have a viscosity index of at least 80 but less than 120. Group III basestocks or base oils contain at least 90 wt % saturated molecules and less than 0.03 wt % sulfur, with a viscosity index of at least 120. In addition to the above formal definitions, some Group I basestocks may be referred to as a Group I+ basestock, which corresponds to a Group I basestock with a VI value of 103 to 108. Some Group II basestocks may be referred to as a Group II+ basestock, which corresponds to a Group II basestock with a VI of at least 113. Some Group III basestocks may be referred to as a Group III+ basestock, which corresponds to a Group III basestock with a VI value of at least 140.

A wide range of petroleum and chemical feedstocks can be processed in accordance with the methods described herein. Suitable feedstocks include whole and reduced petroleum crudes, atmospheric and vacuum residua, atmospheric and vacuum gas oils, and/or other feeds that contain a distillate portion suitable for formation of lubricant base oils. A crude oil fraction is defined herein to include fractions of a whole crude that are generated by distillation of a crude. Crude fractions, unless otherwise specified, are defined herein to include crude oils that have been at least partially processed, such as synthetic crudes and/or other crude oils formed from tar sands or other non-traditional source. The method can be applied to a crude oil or crude fraction from a single source or to a mixture of crude oils and/or crude fractions.

One way of defining a feedstock is based on the boiling range of the feed. One option for defining a boiling range is to use an initial boiling point for a feed and/or a final boiling point for a feed. Another option, which in some instances may provide a more representative description of a feed, is to characterize a feed based on the amount of the feed that boils at one or more temperatures. For example, a "T5" boiling point for a feed is defined as the temperature at which 5 wt % of the feed will boil off. Similarly, a "T50" boiling point is a temperature at 50 wt % of the feed will boil. The percentage of a feed that will boil at a given temperature can he determined by the method specified in ASTM D2887.

Some suitable feeds can correspond to whole crudes. Such feeds can have a broad boiling point range that includes both fuels and lubricant boiling range portions. For more narrowly cut feeds that are still suitable for forming a lubricant oil, typical feeds can include, for example, feeds with an initial boiling point of at least 650° F. (343° C.), or at least 700° F. (371° C.), or at least 750° F. (399° C.). Alternatively, a feed may be characterized using a T5 boiling point, such as a feed with a T5 boiling point of at least 650° F. (343° C.), or at least 700° F. (371° C.), or at least 750° F. (399° C.). In some aspects, the final boiling point and/or T5 boiling point of the feed can be at least 1100° F. (593° C.), such as at least 1150° F. (621° C.) or at least 1200° F. (649° C.). In other aspects, a feed may be used that does not include a large portion of molecules that would traditional be considered as vacuum distillation bottoms. For example, the teed may correspond to a vacuum gas oil feed that has already been separated from a traditional vacuum bottoms portion. Such feeds include, for example, feeds with a final boiling point of 1150° F. (621° C.), or 1100° F. (593° C.) or less, or 1050° F. (566° C.) or less. Alternatively, a feed may be characterized using a T95 boding point, such as a feed with a T95 boiling point of 1150° F. (621° C.) or less, or 1100° F. (593° C.) or less, or 1050° F. (566° C.) or less. An example of a suitable type of feedstock is a wide cut vacuum gas oil (VGO) feed, with a T5 boiling point of at least 700° F. (371° C.) and a T95 boiling point of 1100° F. or less. Optionally, the initial boiling point of such a wide cut VGO feed can be at least 700° F., and/or the final boiling point can be at least 1100° F. It is noted that feeds with still lower initial boiling points and/or T5 boiling points may also be suitable, so long as sufficient higher boiling material is available so that the feedstock is suitable for lubricant base oil production.

If a broader boiling range feed is used, the feedstock can initially be distilled to form a distillate fraction. The cut point for separating a distillate fraction from other lower boiling portions of the feed can correspond to any of the T5 boiling points described above. The distillate fraction can also be separated from a resid or bottoms portion of the feed. The cut point for separating the distillate fraction from the vacuum resid or bottoms portion can be at least 950° F. (510° C.), such as at least 1000° F. (538° C.). Additionally or alternatively, the cut point for separating the distillate fraction from the vacuum resid can be 1100° F. (593° C.) or less.

As an alternative to selecting a cut point for separating a distillate portion from a feedstock based on a temperature, another option is to select a cut point so that the resulting distillate fraction will have a desired kinematic viscosity. For example, if it is desired to form a 100N visgrade base oil from the distillate fraction, the cut point for forming the distillate fraction can be selected so that the kinematic viscosity of the distillate fraction at 100° C. is between 3.8 cSt and 4.2 cSt. If a 150N visgrade base oil is desired, the cut point for forming the distillate fraction can be selected so that the kinematic viscosity of the distillate fraction at 100° C. is between 5.1 cSt and 5.8 cSt. If a 600N visgrade base oil is desired, the cut point for forming the distillate fraction can he selected so that the kinematic viscosity of the distillate fraction at 100° C. is between 13.8 cSt and 16.2 cSt.

Dewaxed Distillate Viscosity Index and VI Potential

The dewaxed distillate viscosity index (DDVI) can be used to predict the VI potential of a feed. The DDVI corresponds to a viscosity index for a distillate portion of a feed (e.g., a 650° F. –1100° F. fraction) prior to performing hydroprocessing and/or aromatic extraction on the distillate portion.

In some embodiments, the feedstock for characterization can correspond to a distillate boiling range feedstock. In other embodiments, one or more separation processes can be used to separate the distillate boiling range portion of a feedstock, such as a portion boiling from at least 650° F. (343° C.) to 1100° F. (593° C.) or less, from the other portions of a feedstock. One example of a possible separation can be to use an atmospheric distillation column to separate lower boiling components of a feedstock from a bottoms portion (or optionally a bottoms portion and one or more other distillate portions). This atmospheric bottoms portion can then be passed into a vacuum distillation column to separate the lower boiling portions from a vacuum bottoms portion. Other potential configurations for separating a desired distillate boiling range portion of a whole or partial crude oil (or another wide boiling feedstock) from other portions of the feedstock can also be used.

After obtaining a distillate fraction and/or forming a distillate fraction from a crude oil or other feedstock, the distillate fraction can then be solvent dewaxed to a desired pour point in order to facilitate determination of the viscosity index for the dewaxed distillate fraction (i.e., the DDVI value). Because the distillate fraction is dewaxed prior to hydroprocessing and/or solvent extraction, the DDVI value will typically be lower than the VI value after hydroprocessing and/or extraction. The DDVI value, however, provides an indication of whether hydroprocessing and/or solvent extraction can provide sufficient VI uplift to produce a base oil having a desired VI value.

Solvent dewaxing typically involves mixing a feed with chilled dewaxing solvent to form an oil-solvent solution. Precipitated wax is thereafter separated by, for example, filtration. The temperature and solvent are selected so that the oil is dissolved by the chilled solvent while the wax is precipitated. Optionally, an aromatics extraction can be performed on the distillate prior to solvent dewaxing, so that the solvent dewaxing is performed on the raffinate from aromatics extractions.

An example of a suitable solvent dewaxing process (including a process for determining a DDVI value) involves the use of a cooling tower where solvent is pre-chilled and added incrementally at several points along the height of the cooling tower. The oil-solvent mixture is agitated during the chilling step to permit substantially instantaneous mixing of the pre-chilled solvent with the oil. The pre-chilled solvent is added incrementally along the length of the cooling tower so as to maintain an average chilling rate at or below 10° F. per minute, usually between 1° F. to 5° F. per minute. The final temperature of the oil-solvent/precipitated wax mixture in the cooling tower will usually be between 0° F. and 50° F. (−17.8° C. to 10° C.). The mixture may then be sent to a scraped surface chiller to separate precipitated wax from the mixture.

Representative dewaxing solvents are aliphatic ketones having 3-6 carbon atoms such as methyl ethyl ketone and methyl isobutyl ketone, low molecular weight hydrocarbons such as propane and butane, and mixtures thereof. The solvents may be mixed with other solvents such as benzene, toluene or xylene.

In general, the amount of solvent added will be sufficient to provide a liquid/solid weight ratio between the range of 5/1 and 20/1 at the dewaxing temperature and a solvent/oil volume ratio between 1.5/1 to 5/1. The solvent dewaxed oil is typically dewaxed to a desired pour point. For the dewaxed distillate viscosity index test described below, one option is to use solvent dewaxing to achieve a pour point value of −9° C. Alternatively, the solvent dewaxing can be used to achieve other convenient pour points that are useful for characterizing the distillate in order to determine a viscosity index at a given temperature, such as a viscosity index at −9° C.

Determining a VI value for a dewaxed distillate portion at a pour point can be determined by any convenient method. One option is to measure the VI value for a dewaxed distillate fraction at the desired or target pour point. After forming the distillate portion, the distillate portion can be solvent dewaxed as described above. The severity of the solvent dewaxing can be sufficient for achieving a desired pour point, such as 0° C. or less, −6° C. or less, or −9° C. or less. The viscosity index of the dewaxed distillate fraction can then be directly measured, such as by measuring the viscosity of the dewaxed distillate at two different temperatures. Any convenient temperatures can be selected, such as 40° C., 100° C., 130° C., or other convenient temperatures.

Differential Scanning Calorimetry for Wax Content

It has been discovered that wax content as determined by differential scanning calorimetry (DSC), in combination with several other measured characteristics of a distillate fraction, can be used to predict the DDVI value at a target pour point for a feedstock. In some aspects, detailed information regarding the composition of a feedstock may not be available. In such aspects, the wax content can be derived based on the DSC cooling and heating curves for a feedstock sample.

The DSC cooling and heating curves for a feedstock are heat flow as a function of temperature. The DSC curve is determined by first heating the feedstock sample to a temperature sufficient to melt all the residual wax contained in the feedstock. The measurement is typically preferably started at 80° C. but can vary based on the feed, such as starting at a temperature of 100° C. or 120° C. The feedstock sample is then cooled at a cooling rate of 0.5° C. to 20° C. per minute and preferably 1° C. to 10° C. per minute. For the examples described herein, the feedstock sample was cooled at 3° C. per minute. The feedstock is cooled to a temperature sufficient to completely solidify the feedstock sample. For most feedstock samples, this will be between −10° C. to −80° C.

The DSC heating curve is then created by heating at a rate of approximately 5° C. to 20° C. per minute, such as about 10° C. per minute. Preferably, the cooling and heating rates should be kept consistent to keep the correlation accurate. This was done with a commercially available DSC unit but any equivalent machine could be used.

The heating and cooling curves described above can then be converted to wax content. A first-principles translation of the cooling curve to the physical amount of wax corresponding to these phase changes would require detailed knowledge of the sample composition and the corresponding heats of fusion for each molecular species. Since such detailed information may be unavailable, an empirical correlation relating the wax content of representative feedstocks used for commercial lubricant base oil production to DSC heat input as a function of temperature can be determined. This correlation can then be used to calculate the wax distribution versus temperature of test samples from their experimentally measured heating curves. A person skilled in the art with the benefit of this description could create a new fundamentally-based model for this application. The operative equation is:

$$W = \Delta H / A(T) \quad (1)$$

In the above equation, W is the wax content of a sample. $\Delta H$ represents the amount of heat absorbed by the droplet of sample in the DSC when a freezing phase transition occurs, as indicated by the presence of a peak in the cooling (or heating) trace. $A(T)$ is a scaling factor that can optionally be dependent on the temperature at which the freezing transition occurs. Without being bound by any particular theory, it is believed that the above relationship is suitable for determining a wax content base in part on the nature of the freezing transition during heating and/or cooling. A DSC performs measurements on a droplet of a wax-containing sample. It is believed that the heat of fusion for the wax within the droplet is the dominant contribution to the heat of fusion for the entire droplet. As a result, the heat of fusion for the entire droplet can be related by a scaling factor of some type to the amount of wax in the droplet.

In Equation (1), the scaling factor $A(T)$ is shown as a function of temperature. Without being bound by any particular theory, it is believed that a scaling factor having the form $A(T) = a_1 + a_2 T$ is one suitable option for a scaling factor. Other functional forms may also be suitable.

Correlation of DDVI with Feed Distillate Properties

In addition to determining a wax content at a temperature for a distillate portion of a feedstock, a characteristic boiling point, a characteristic viscosity, and refractive index can be determined for the distillate portion of a feedstock. These measured values can then be used to predict a DDVI value at a target pour point for the feedstock. The characteristic boiling point can be useful in the model for determining that a sample has an appropriate boiling range for forming a lubricant base oil. The refractive index can be useful for determining the relative yield from a solvent extraction and/or hydroprocessing process. The characteristic viscosity can be useful for determining the viscosity of the resulting lubricant base oil.

In some aspects, the characteristic boiling point for a distillate sample can correspond to a volume average boiling point. The volume average boiling point can be determined, for example, by averaging a plurality of intermediate distillation boiling points as determined by ASTM D2887 or another convenient method. For example, a Tv10 boiling point can correspond to a temperature where 10 vol % of a sample will boil. The volume average boiling point for a sample can be determined based an average of the Tv10, Tv30, Tv50, Tv70, and Tv90 boiling points. The characteristic viscosity for a distillate sample can correspond to a kinematic viscosity. The kinematic viscosity can be measured at any convenient temperature, such as a kinematic viscosity at 40° C. or at 100° C. Kinematic viscosity can be determined, for example, according to ASTM D445. The refractive index can correspond to a refractive index at a specified temperature, such as a refractive index at 75° C. The refractive index can be determined, for example, according to ASTM D1218.

As an example, it has been determined that the DSC wax content at −9° C., the volume-average boiling point, the kinematic viscosity at 100° C., and the refractive index at 75° C. can be used to predict a DDVI value based on the relationship in Equation 2:

$$DDVI@-9°\ C.=A_{10}-A_{11}*XRI-A_{12}*e^{a_{121}DWX09^{a_{122}}}*(\ln(Ykv100+0.6))^{a_{123}}+A_{13}*ZVABP-A_{14}*\ln(Ykv100+0.6))$$

In Equation (2), XRI is the refractive index at 75° C.; Ykv100 is the kinematic viscosity at 100° C.; ZVABP is the volume-average boiling point; and DWX09 is the wax as measured by DSC at −9° C. The parameters $A_{10}$, $A_{11}$, $A_{12}$, $A_{13}$, $A_{14}$, $a_{121}$, $a_{122}$, and $a_{123}$ were all determined via regression over a database of previously measured values for a variety of distillate feedstocks. In this Examples provided herein, a single set of parameters was used. In some alternative aspects, a different set of parameters can be determined for each viscosity grade of base oil that is considered for production from a given feedstock.

FIG. 1 shows an example of DDVI values predicted using Equation (2) above versus measured DDVI values for a variety of feedstocks. As shown in FIG. 1, the predicted DDVI values correlate strongly with the measured values. This demonstrates the effectiveness of the discovered correlation for providing a rapid method of predicting DDVI values.

Figure 2:
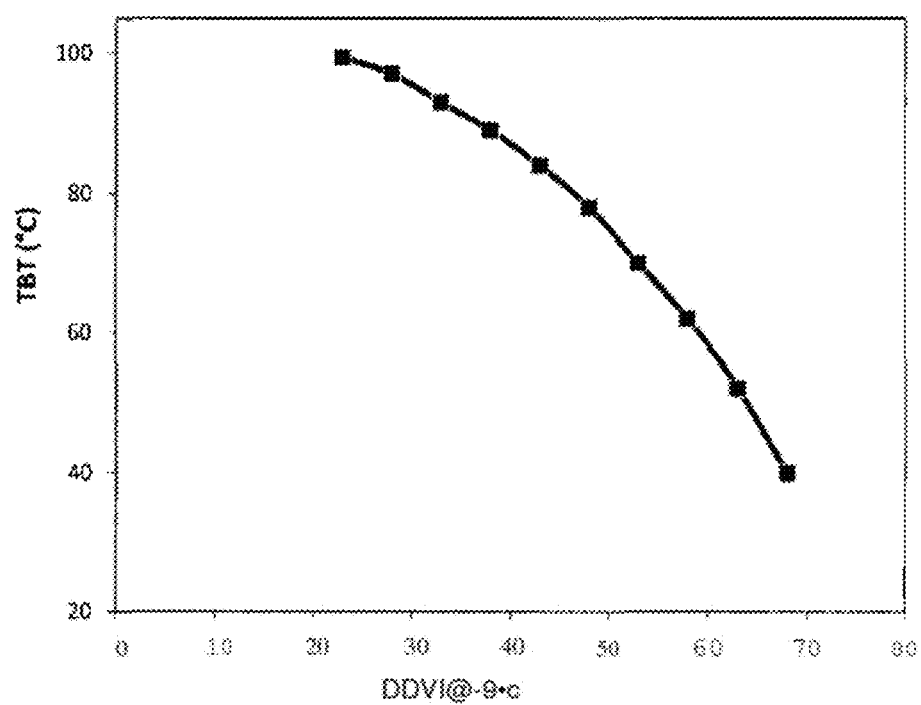
FIGS. 2 and 3 show examples of a correlation between feedstock DDVI values and solvent extraction severity for forming a lubricant base oil with a target VI value.
Figure 3:
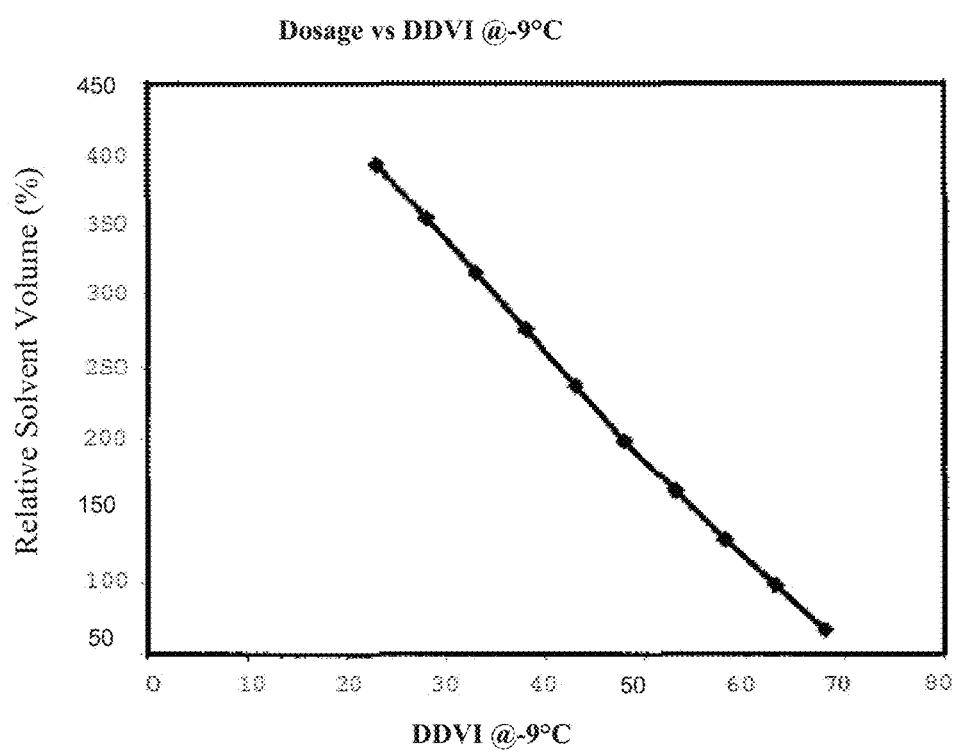

FIGS. 2 and 3 demonstrate how a predicted DDVI value can be used to determine the suitability of a feedstock for lubricant base oil production. In FIG. 2, the tower bottoms temperature (TBT) for a solvent extraction process performed on a variety of feedstocks is shown relative to DDVI for the feedstock. Increasing the TBT for a solvent extraction process corresponds to an increase in extraction severity due to increased solvency, with a corresponding decrease in yield. In the example shown in FIG. 2, the distillate portion of a feedstock is solvent extracted so that the base oil formed after solvent dewaxing will correspond to a 600 N base oil with a 95 VI. The extractor used for the example in FIG. 2 had 5 theoretical stages. The extraction was performed at a constant solvent treat dosage of 164 vol % (relative to the volume of feedstock). The extraction solvent was n-methylpyrrolidone (NMP) with 1.5 wt % $H_2O$ and a 10° C. temperature gradient. The target pour point in the subsequent solvent dewaxing process was −9° C.

In the example shown in FIG. 2, feedstocks with higher DDVI values require a corresponding lower severity (i.e., lower TBT) to achieve a VI of 95 for a base oil having a pour point of −9° C. It is also noted that the ability to increase temperature to process feedstocks with lower DDVI values is limited. FIG. 2 shows that the temperature required to achieve a base oil with 95 VI levels off as the feedstock DDVI decreases toward 20. Below a DDVI of 10, however, further increases in temperature are not effective for achieving a base oil VI of 95. The particular threshold DDVI that is needed to achieve a desired base oil VI can vary depending on a variety of factors, such as the viscosity of the desired base oil and the desired VI. In various aspects, the threshold DDVI for forming a desired basestock can be a DDVI of at least 0, or at least 10, or at least 20.

FIG. 3 provides a different example for demonstrating the relationship between DDVI and extraction severity. In FIG. 3, instead of varying the tower bottoms temperature (TBT), the TBT is held constant at 70° C. while the volume of solvent used (relative to the volume of feedstock) is varied. Increasing the relative volume of solvent provides another option for increasing the severity of an extraction process. FIG. 3 shows the volume of solvent required relative to the DDVI of the feed for the same group of feedstocks used in FIG. 2. Similar to FIG. 2, feedstocks with lower DDVI values require greater extraction severity to achieve the target VI of 95 for a base oil with a −9° C. pour point.

Lubricant Base oil Production: Solvent Processing and Hydroprocessing

Two types of solvent processing can typically be performed on a feedstock to form a lubricant base oil. The first type of solvent processing is a solvent extraction to reduce the aromatics content and/or the amount of polar molecules. The second type of solvent processing is solvent dewaxing, as described above.

A solvent extraction process selectively dissolves aromatic components to form an aromatics-rich extract phase while leaving the more paraffinic components in an aromatics-poor raffinate phase. Naphthenes are distributed between the extract and raffinate phases. Typical solvents for solvent extraction include phenol, furfural and N-methyl pyrrolidone. By controlling the solvent to oil ratio, extraction temperature and method of contacting distillate to be extracted with solvent, one can control the degree of separation between the extract and raffinate phases. Any convenient type of liquid-liquid extractor can be used, such as a counter-current liquid-liquid extractor. Depending on the initial concentration of aromatics in the deasphalted bottoms, the raffinate phase can have an aromatics content of about 5 wt % to about 25 wt %. For typical feeds, the aromatics contents will be at least about 10 wt %.

Optionally, raffinate yield may be adjusted by controlling extraction conditions, for example, by lowering the solvent to oil treat ratio and/or decreasing the extraction temperature. It is noted that adjusting the extraction conditions to increase the VI of a base oil can typically correspond to higher severity conditions that will reduce raffinate yield. The raffinate from the solvent extraction unit can then be solvent dewaxed under solvent dewaxing conditions to remove hard waxes from the raffinate.

Solvent dewaxing typically involves mixing the raffinate feed from the solvent extraction unit with chilled dewaxing solvent to form an oil-solvent solution. Precipitated wax is thereafter separated by, for example, filtration. The temperature and solvent are selected so that the oil is dissolved by the chilled solvent while the wax is precipitated. Solvent dewaxing can be performed in a manner similar to the solvent dewaxing processes described above.

In some aspects, a feed may be hydroprocessed in addition to or in place of solvent extraction and/or solvent dewaxing. The hydroprocessing can include one or more of hydrotreatment, catalytic dewaxing, and/or hydrofinishing. In aspects where more than one type of hydroprocessing is performed, the effluent from a first type of hydroprocessing can optionally be separated prior to the second type of catalytic processing. For example, after a hydrotreatment or hydrofinishing process, a gas-liquid separation can be performed to remove light ends, $H_2S$, and/or $NH_3$ that may have formed.

Hydrotreatment is typically used to reduce the sulfur, nitrogen, and aromatic content of a feed. The catalysts used for hydrotreatment of the heavy portion of the crude oil from the flash separator can include conventional hydroprocessing catalysts, such as those that comprise at least one Group VIII non-noble metal (Columns 8-10 of IUPAC periodic table), preferably Fe, Co, and/or Ni, such as Co and/or Ni; and at least one Group VI metal (Column 6 of IUPAC periodic table), preferably Mo and/or W. Such hydroprocessing catalysts optionally include transition metal sulfides that are impregnated or dispersed on a refractory support or carrier such as alumina and/or silica. The support or carrier itself typically has no significant/measurable catalytic activity. Substantially carrier- or support-free catalysts, commonly referred to as bulk catalysts, generally have higher volumetric activities than their supported counterparts.

The catalysts can either be in bulk form or in supported form. In addition to alumina and/or silica, other suitable support/carrier materials can include, but are not limited to, zeolites, titania, silica-titania, and titania-alumina. Suitable aluminas are porous aluminas such as gamma or eta having average pore sizes from 50 to 200 Å, or 75 to 150 Å; a surface area from 100 to 300 $m^2/g$, or 150 to 250 $m^2/g$; and a pore volume of from 0.25 to 1.0 $cm^3/g$, or 0.35 to 0.8 $cm^3/g$. More generally, any convenient size, shape, and/or pore size distribution for a catalyst suitable for hydrotreatment of a distillate (including lubricant base oil) boiling range feed in a conventional manner may be used. It is within the scope of the present disclosure that more than one type of hydroprocessing catalyst can be used in one or multiple reaction vessels.

The at least one Group VIII non-noble metal, in oxide form, can typically be present in an amount ranging from about 2 wt % to about 40 wt %, preferably from about 4 wt % to about 15 wt %. The at least one Group VI metal, in oxide form, can typically be present in an amount ranging from about 2 wt % to about 70 wt %, preferably for supported catalysts from about 6 wt % to about 40 wt % or from about 10 wt % to about 30 wt %. These weight percents are based on the total weight of the catalyst. Suitable metal catalysts include cobalt/molybdenum (1-10% Co as oxide, 10-40% Mo as oxide), nickel/molybdenum (1-10% Ni as oxide, 10-40% Co as oxide), or nickel/tungsten (1-10% Ni as oxide, 10-40% W as oxide) on alumina, silica, silica-alumina, or titania.

The hydrotreatment is carried out in the presence of hydrogen. A hydrogen stream is, therefore, fed or injected into a vessel or reaction zone or hydroprocessing zone in which the hydroprocessing catalyst is located. Hydrogen, which is contained in a hydrogen "treat gas," is provided to the reaction zone. Treat gas, as referred to in this disclosure, can be either pure hydrogen or a hydrogen-containing gas, which is a gas stream containing hydrogen in an amount that is sufficient for the intended reaction(s), optionally including one or more other gasses (e.g., nitrogen and light hydrocarbons such as methane), and which will not adversely interfere with or affect either the reactions or the products. Impurities, such as $H_2S$ and $NH_3$ are undesirable and would typically be removed from the treat gas before it is conducted to the reactor. The treat gas stream introduced into a reaction stage will preferably contain at least about 50 vol. % and more preferably at least about 75 vol. % hydrogen.

Hydrogen can be supplied at a rate of from about 100 SCF/B (standard cubic feet of hydrogen per barrel of feed) (17 $Nm^3/m^3$) to about 1500 SCF/B (253 $Nm^3/m^3$). Preferably, the hydrogen is provided in a range of from about 200 SCF/B (34 $Nm^3/m^3$) to about 1200 SCF/B (202 $Nm^3/m^3$). Hydrogen can be supplied co-currently with the input feed to the hydrotreatment reactor and/or reaction zone or separately via a separate gas conduit to the hydrotreatment zone.

Hydrotreating conditions can include temperatures of 200° C. to 450° C., or 315° C. to 425° C.; pressures of 250 psig (1.8 MPag) to 5000 psig (34.6 MPag) or 300 psig (2.1 MPag) to 3000 psig (20.8 MPag); liquid hourly space velocities (LHSV) of 0.1 $hr^{-1}$ to 10 $hr^{-1}$; and hydrogen treat rates of 200 scf/B (35.6 $m^3/m^3$) to 10,000 scf/B (1781 $m^3/m^3$), or 500 (89 $m^3/m^3$) to 10,000 scf/B (1781 $m^3/m^3$).

Another type of hydroprocessing can be catalytic dewaxing. Catalytic dewaxing can be used to improve the cold flow properties of a high viscosity base oil, and can potentially also perform some heteroatom removal and aromatic saturation. Suitable dewaxing catalysts can include molecular sieves such as crystalline aluminosilicates (zeolites). In an embodiment, the molecular sieve can comprise, consist essentially of, or be ZSM-5, ZSM-22, ZSM-23, ZSM-35, ZSM-48, zeolite Beta, or a combination thereof, for example ZSM-23 and/or ZSM-48, or ZSM-48 and/or zeolite Beta. Optionally but preferably, molecular sieves that are selective for dewaxing by isomerization as opposed to cracking can be used, such as ZSM-48, zeolite Beta, ZSM-23, or a combination thereof. Additionally or alternately, the molecular sieve can comprise, consist essentially of, or be a 10-member ring 1-D molecular sieve. Examples include EU-1, ZSM-35 (or ferrierite), ZSM-11, ZSM-57, NU-87, SAPO-11, ZSM-48, ZSM-23, and ZSM-22. Preferred materials are EU-2, EU-11, ZBM-30, ZSM-48, or ZSM-23. ZSM-48 is most preferred. Note that a zeolite having the ZSM-23 structure with a silica to alumina ratio of from about 20:1 to about 40:1 can sometimes be referred to as SSZ-32. Other molecular sieves that are isostructural with the above materials include Theta-1, NU-10, EU-13, KZ-1, and NU-23. Optionally but preferably, the dewaxing catalyst can include a binder for the molecular sieve, such as alumina, titania, silica, silica-alumina, zirconia, or a combination thereof, for example alumina and/or titania or silica and/or zirconia and/or titania.

Preferably, the dewaxing catalysts used in processes according to the disclosure are catalysts with a low ratio of silica to alumina. For example, for ZSM-48, the ratio of silica to alumina in the zeolite can be less than about 200:1, such as less than about 110:1, or less than about 100:1, or less than about 90:1, or less than about 75:1. In various embodiments, the ratio of silica to alumina can be from 50:1 to 200:1, such as 60:1 to 160:1, or 70:1 to 100:1.

In various embodiments, the catalysts according to the disclosure further include a metal hydrogenation component. The metal hydrogenation component is typically a Group VI and/or a Group VIII metal. Preferably, the metal hydrogenation component is a Group VIII noble metal. Preferably, the metal hydrogenation component is Pt, Pd, or a mixture thereof. In an alternative preferred embodiment, the metal hydrogenation component can be a combination of a non-noble Group VIII metal with a Group VI metal. Suitable combinations can include Ni, Co, or Fe with Mo or W, preferably Ni with Mo or W.

The metal hydrogenation component may be added to the catalyst in any convenient manner. One technique for adding the metal hydrogenation component is by incipient wetness. For example, after combining a zeolite and a binder, the combined zeolite and binder can be extruded into catalyst particles. These catalyst particles can then be exposed to a solution containing a suitable metal precursor. Alternatively, metal can be added to the catalyst by ion exchange, where a metal precursor is added to a mixture of zeolite (or zeolite and binder) prior to extrusion.

The amount of metal in the catalyst can be at least 0.1 wt % based on catalyst, or at least 0.15 wt %, or at least 0.2 wt %, or at least 0.25 wt %, or at least 0.3 wt %, or at least 0.5 wt % based on catalyst. The amount of metal in the catalyst can be 20 wt % or less based on catalyst, or 10 wt % or less, or 5 wt % or less, or 2.5 wt % or less, or 1 wt % or less. For embodiments where the metal is Pt, Pd, another Group VIII noble metal, or a combination thereof, the amount of metal can be from 0.1 to 5 wt %, preferably from 0.1 to 2 wt %, or 0.25 to 1.8 wt %, or 0.4 to 1.5 wt %. For embodiments where the metal is a combination of a non-noble Group VIII metal with a Group VI metal, the combined amount of metal can be from 0.5 wt % to 20 wt %, or 1 wt % to 15 wt %, or 2.5 wt % to 10 wt %.

The dewaxing catalysts can also include a binder. In some embodiments, the dewaxing catalysts can be formulated using a low surface area binder, where a low surface area binder represents a binder with a surface area of 100 m$^2$/g or less, or 80 m$^2$/g or less, or 70 m$^2$/g or less. The amount of zeolite in a catalyst formulated using a binder can be from about 30 wt % zeolite to 90 wt % zeolite relative to the combined weight of binder and zeolite. Preferably, the amount of zeolite is at least about 50 wt % of the combined weight of zeolite and binder, such as at least about 60 wt % or from about 65 wt % to about 80 wt %. A zeolite can be combined with binder in any convenient manner.

Process conditions in a catalytic dewaxing zone in a sour environment can include a temperature of from 200 to 450° C., preferably 270 to 400° C., a hydrogen partial pressure of from 1.8 MPag to 34.6 MPag (250 psig to 5000 psig), preferably 4.8 MPag to 20.8 MPag, and a hydrogen circulation rate of from 35.6 m$^3$/m$^3$ (200 SCF/B) to 1781 m$^3$/m$^3$ (10,000 scf/B), preferably 178 m$^3$/m$^3$ (1000 SCF/B) to 890.6 m$^3$/m$^3$ (5000 SCF/B). In still other embodiments, the conditions can include temperatures in the range of about 600° F. (343° C.) to about 815° F. (435° C.), hydrogen partial pressures of from about 500 psig to about 3000 psig (3.5 MPag-20.9 MPag), and hydrogen treat gas rates of from about 213 m$^3$/m$^3$ to about 1068 m$^3$/m$^3$ (1200 SCF/B to 6000 SCF/B). These latter conditions may be suitable, for example, if the dewaxing stage is operating under sour conditions. The LHSV can be from about 0.2 h$^{-1}$ to about 10 h$^{-1}$, such as from about 0.5 h$^{-1}$ to about 5 h$^{-1}$ and/or from about 1 h$^{-1}$ to about 4 h$^{-1}$.

Still another type of hydroprocessing can be hydrofinishing or aromatic saturation. Hydrofinishing and/or aromatic saturation catalysts can include catalysts containing Group VI metals, Group VIII metals, and mixtures thereof. In an embodiment, preferred metals include at least one metal sulfide having a strong hydrogenation function. In another embodiment, the hydrofinishing catalyst can include a Group VIII noble metal, such as Pt, Pd, or a combination thereof. The mixture of metals may also be present as bulk metal catalysts wherein the amount of metal is about 30 wt. % or greater based on catalyst. Suitable metal oxide supports include low acidic oxides such as silica, alumina, silica-aluminas or titanic, preferably alumina. The preferred hydrofinishing catalysts for aromatic saturation will comprise at least one metal having relatively strong hydrogenation function on a porous support. Typical support materials include amorphous or crystalline oxide materials such as alumina, silica, and silica-alumina. The support materials may also be modified, such as by halogenation, or in particular fluorination. The metal content of the catalyst is often as high as about 20 weight percent for non-noble metals. In an embodiment, a preferred hydrofinishing catalyst can include a crystalline material belonging to the M41S class or family of catalysts. The M41S family of catalysts are mesoporous materials having high silica content. Examples include MCM-41, MCM-48 and MCM-50. A preferred member of this class is MCM-41. If separate catalysts are used for aromatic saturation and hydrofinishing, an aromatic saturation catalyst can be selected based on activity and/or selectivity for aromatic saturation, while a hydrofinishing catalyst can be selected based on activity for improving product specifications, such as product color and polynuclear aromatic reduction.

Hydrofinishing conditions can include temperatures from about 125° C. to about 425° C., preferably about 180° C. to about 280° C., a hydrogen partial pressure from about 500 psig (3.4 MPa) to about 3000 psig (20.7 MPa), preferably about 1500 psig (10.3 MPa) to about 2500 psig (17.2 MPa), and liquid hourly space velocity from about 0.1 hr$^{-1}$ to about 5 hr$^{-1}$ LHSV, preferably about 0.5 hr$^{-1}$ to about 1.5 hr$^{-1}$. Additionally, a hydrogen treat gas rate of from 35.6 m$^3$/m$^3$ to 1781 m$^3$/m$^3$ (200 SCF/B to 10,000 SCF/B) can be used.

Detection of Filterability Based on DSC Cooling Trace

In addition to using DSC for rapid determination of a DDVI value for a distillate portion of a feedstock, DSC can also be used for detection of wax content during and/or after a solvent dewaxing process. Wax detection during a process can be valuable for determining if wax ingress is occurring, such as due to a hole in a filter cloth, a leak in a valve, or based on another type of unexpected process failure. Wax detection after a process can be valuable for determining whether a dewaxed sample (such as a Group I lubricant base oil) can pass a filterability test.

For detection of wax ingress during a process and/or determining wax content of a sample after dewaxing, a DSC cooling trace can be generated as described above. However, instead of using the cooling trace to determine a wax content, either an average slope from the liquid to solid transition region of the cooling trace or a maximum slope of the cooling trace is determined. Samples with low wax content will exhibit a steeper slope, while samples with higher wax content will have a smaller magnitude slope and/or a lower maximum slope value.

Use of DSC for wax detection is in contrast to conventional wax detection methods during solvent processing, which rely on a filterability test. A filterability test, such as a filterability test according at ASTM D6794, typically takes roughly a day to complete, meaning that a substantial amount of base oil production can occur before a problem is detected. Use of DSC for wax detection provides an alternative wax detection method that can be performed in roughly 1-2 hours, instead of requiring a day or more.

An additional benefit of using DSC for wax detection can be detection of amounts of wax in a sample that will pass a filterability test but that may cause haze formation. The conventional method for detection of haze in a sample is to perform a flocculation test. However, a flocculation test is qualitative, and may not reliably determine whether a sample will be haze free. This is due in part to the long times required for haze to appear in some samples.

Figure 5:
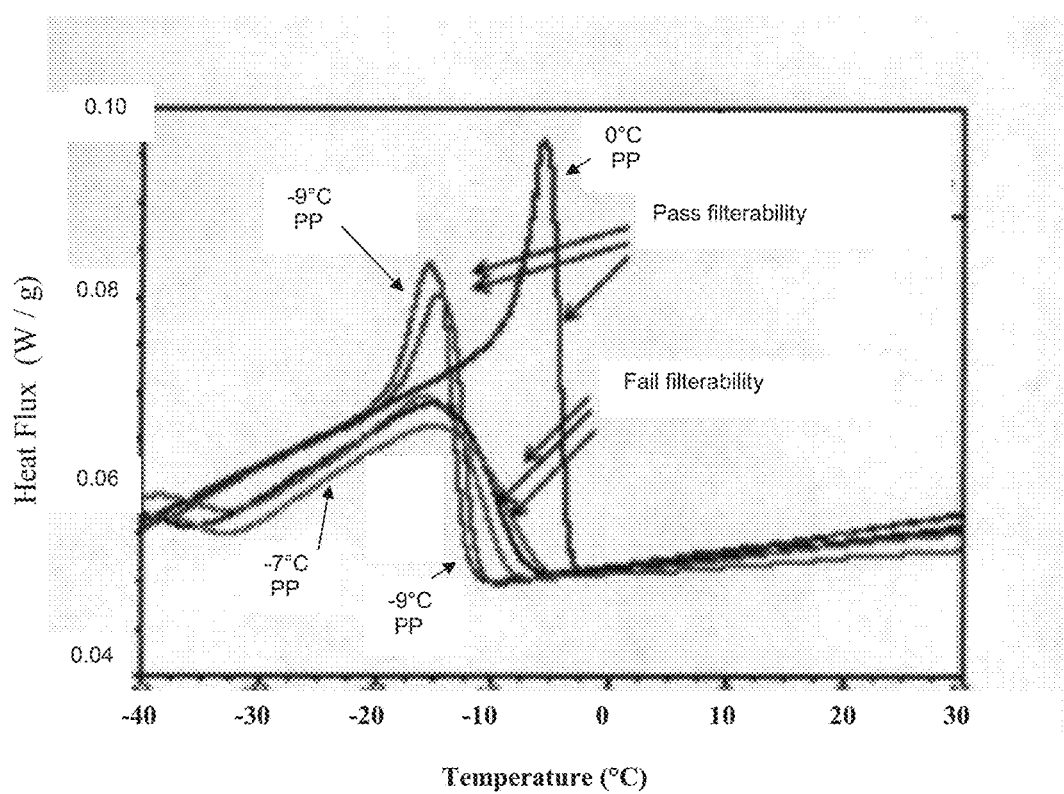
FIGS. 5 and 6 show examples of DSC cooling traces for a variety of lubricant base oils.

FIG. 5 shows an example of how a DSC cooling trace can be used to determine the filterability of a potential base oil sample. FIG. 5 shows DSC cooling traces for various solvent processed base oil samples having a pour point of 0° C., −7° C., or −9° C. The samples shown in FIG. 5 having a sharper wax transition (i.e., a larger magnitude slope) in the cooling trace correspond to samples that passed the filterability test. The samples in FIG. 5 having a lower magnitude slope correspond to samples that failed a filterability test. The difference between the samples that pass filterability and that do not pass filterability can be determined based on an average slope within the wax onset region of the cooling trace, based on a maximum value of the derivative in the wax onset region, or a combination thereof. In a typical cooling trace, the slope in the wax onset region will typically have a negative value. Using the magnitude of the slope allows passing samples to be described based on having a slope magnitude larger than a threshold value. Those of skill in the art will understand that the slope itself, which has a negative value, could equally be used to determine samples that satisfy the filterability test. It is noted that for a lubricant base oil type sample, the pour point of the base oil does not impact the threshold for determining the difference between a base oil that will pass a filterability test and a base oil that will fail the test.

In various aspects, a sample that has a sufficiently low wax content (such as a sample that can pass a filterability test) can correspond to a sample with a slope in the DSC cooling trace curve with a magnitude of at least 0.0005, or at least 0.008, or at least 0.01. The slope can correspond to an average slope or a maximum slope, such as a maximum derivative value.

Figure 6:
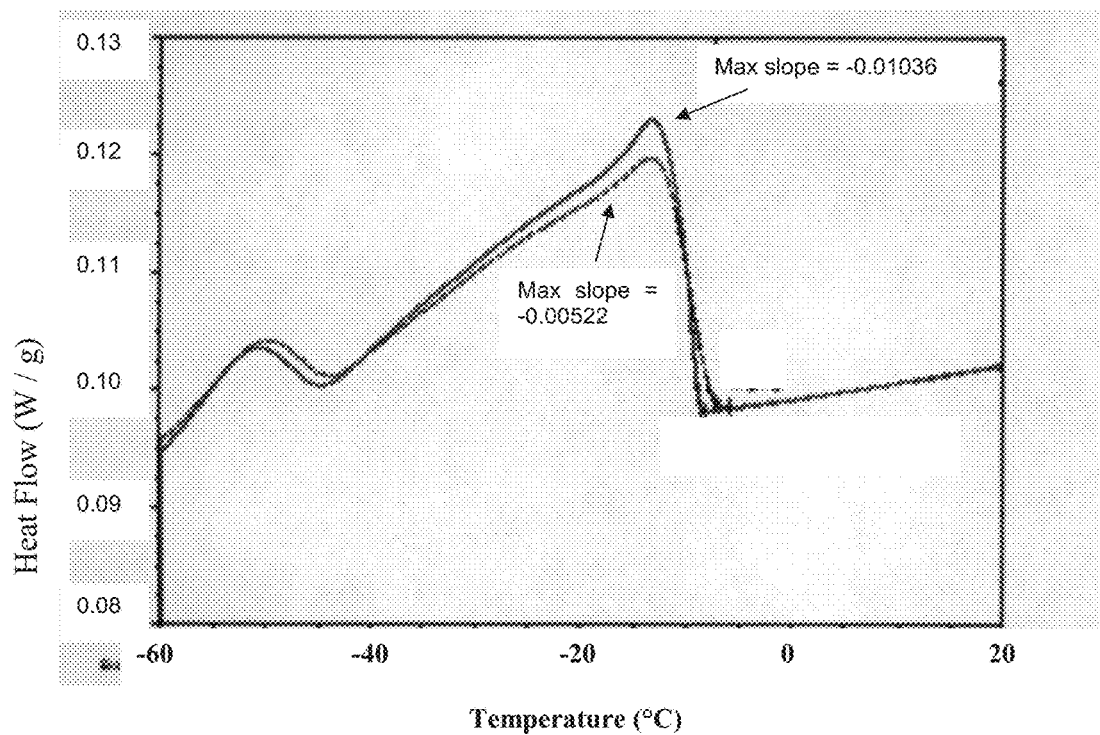

FIG. 6 shows DSC cooling traces for two 600 N base oil samples that were tested to determine if the samples were susceptible to forming haze. For detection of haze formation, the slope condition can be different from determining suitability for passing filterabilty. In various aspects, a sample that will not develop haze can correspond to a sample with a slope magnitude of at least 0.008 W/g° C., or at least 0.01 W/g° C. As shown in FIG. 6, although the cooling traces for the two 600 N base oil samples appear similar, the slopes from the cooling trace allow the base oil that was observed to form haze to be distinguished from the base oil that does not form haze.

Additional Embodiments

Embodiment 1. An method for determining feedstock quality for lubricant base oil production, comprising: determining a wax content of a distillate feedstock fraction by differential scanning calorimetry; obtaining a characteristic boiling point, a characteristic viscosity, and a refractive index for the distillate feedstock fraction; calculating a distillate dewaxed viscosity index (DDVI) at a DDVI-temperature for the distillate feedstock fraction based on the determined wax content and at least two of the obtained characteristic boiling point, the obtained characteristic viscosity, and the obtained refractive index, the calculated DDVI being at least 0 at the DDVI-temperature; and processing the feedstock to form a lubricant base oil having a viscosity index of at least 80 and a pour point of 0° C. or less.

Embodiment 2. The method of Embodiment 1, wherein the DDVI-temperature is −9° C.

Embodiment 3. The method of any of the above embodiments, wherein obtaining at least one of the characteristic boiling point, the characteristic viscosity, and the refractive index comprises measuring the at least one of the characteristic boiling point, the characteristic viscosity, and the refractive index.

Embodiment 4. A method for determining feedstock quality for lubricant base oil production, comprising: determining a wax content of a distillate feedstock fraction by differential scanning calorimetry; measuring at least two of a characteristic boiling point, a characteristic viscosity, and a refractive index for the distillate feedstock fraction; calculating a distillate dewaxed viscosity index (DDVI) at −9° C. for the distillate feedstock fraction based on the determined wax content and the measured at least two of the characteristic boiling point, the characteristic viscosity, and the refractive index, the calculated DDVI being at least 0 at −9° C.; and processing the feedstock to form a lubricant base oil having a viscosity index of at least 80 and a pour point of 0° C. or less.

Embodiment 5. The method of any of the above embodiments, wherein the wax content of the distillate feedstock fraction is determined based on the relationship $W=\Delta H/A(T)$, where W is the wax content, $\Delta H$ is a heat of fusion, T is a temperature where a freezing transition occurs, and $A(T)$ is a scaling factor.

Embodiment 6. The method of any of the above embodiments, wherein the characteristic viscosity comprises a kinematic viscosity, the kinematic viscosity optionally being a kinematic viscosity at 40° C. or 100° C.

Embodiment 7. The method of any of the above embodiments, wherein the characteristic boiling point comprises a volume average boiling point.

Embodiment 8. The method of any of the above embodiments, wherein the refractive index comprises a refractive index at 75° C.

Embodiment 9. The method of any of the above embodiments, wherein the distillate dewaxed viscosity index at the DDVI temperature is calculated based on the formula: $DDVI=A_{10}-A_{11}*XRI-A_{12}*e^{a121}DWX09^{a122}*(\ln(Ykv100+0.6))^{a123}+A_{13}*ZVABP-A_{14}*\ln(\ln(Ykv100+0.6))$.

Embodiment 10. The method of any of the above embodiments, wherein the distillate feedstock fraction comprises a fraction having a T5 boiling point of at least 650° F., a T95 boiling point of 1100° F. or less, or a combination thereof.

Embodiment 11. The method of any of the above embodiments, wherein processing a feedstock comprises solvent processing, hydroprocessing, or a combination thereof.

Embodiment 12. The method of any of the above embodiments, wherein processing a feedstock further comprises determining a suitability of the lubricant base oil for satisfying at least one of a filterability test or a flocculation test based on determining a slope of a cooling trace measured by differential scanning calorimetry.

Embodiment 13. The method of Embodiment 12, wherein the suitability of the lubricant base oil is based on the determined slope of the cooling trace being at least 0.008 W/g° C., or at least 0.01 W/g° C.

Embodiment 14. A lubricant base oil made according to the method of any of Embodiments 1-13.

When numerical lower limits and numerical upper limits are listed herein, ranges from any lower limit to any upper limit are contemplated. While the illustrative embodiments of the disclosure have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

The present invention has been described above with reference to numerous embodiments and specific examples. Many variations will suggest themselves to those skilled in this art in light of the above detailed description. All such obvious variations are within the full intended scope of the appended claims.

The invention claimed is:

1. A method for determining feedstock quality for lubricant base oil production, comprising:
   determining a wax content of a distillate feedstock fraction by differential scanning calorimetry;
   obtaining a characteristic boiling point, a characteristic viscosity, and a refractive index for the distillate feedstock fraction;
   calculating a distillate dewaxed viscosity index (DDVI) at a DDVI-temperature for the distillate feedstock fraction based on the determined wax content and at least two of the obtained characteristic boiling point, the obtained characteristic viscosity, and the obtained refractive index, the calculated DDVI being at least 0 at the DDVI-temperature; and
   processing the feedstock to form a lubricant base oil having a viscosity index of at least 80 and a pour point of 0° C. or less.

2. The method of claim 1, wherein the DDVI-temperature is −9° C.

3. The method of claim 1, wherein the wax content of the distillate feedstock fraction is determined based on the relationship $W = \Delta H / A(T)$, where W is the wax content, $\Delta H$ is a heat of fusion, T is a temperature where a freezing transition occurs, and A(T) is a scaling factor.

4. The method of claim 1, wherein obtaining at least one of the characteristic boiling point, the characteristic viscosity, and the refractive index comprises measuring the at least one of the characteristic boiling point, the characteristic viscosity, and the refractive index.

5. The method of claim 1, wherein the characteristic viscosity comprises a kinematic viscosity at 40° C.

6. The method of claim 1, wherein the characteristic viscosity comprises a kinematic viscosity at 100° C.

7. The method of claim 1, wherein the characteristic boiling point comprises a volume average boiling point.

8. The method of claim 1, wherein the refractive index comprises a refractive index at 75° C.

9. The method of claim 1, wherein the distillate dewaxed viscosity index at the DDVI temperature is calculated based on the formula:

$$DDVI = A_{10} - A_{11} \cdot XRI - A_{12} \cdot e^{a121 DWX09^{a122}} \cdot (\ln(Ykv100+0.6))^{a123} + A_{13} \cdot ZVABP - A_{14} \cdot \ln(\ln(Ykv100+0.6)).$$

10. The method of claim 1, wherein the distillate feedstock fraction comprises a fraction having a T5 boiling point of at least 650° F., a T95 boiling point of 1100° F. or less, or a combination thereof.

11. The method of claim 1, wherein processing the feedstock comprises solvent processing, hydroprocessing, or a combination thereof.

12. The method of claim 1, wherein processing the feedstock further comprises determining a suitability of the lubricant base oil for satisfying at least one of a filterability test or a flocculation test based on determining a slope of a cooling trace measured by differential scanning calorimetry.

13. The method of claim 12, wherein the suitability of the lubricant base oil is based on the determined slope of the cooling trace being at least 0.008 W/g° C.

14. The method of claim 12, wherein the suitability of the lubricant base oil is based on the determined slope of the cooling trace being at least 0.01 W/g° C.

15. A method for determining feedstock quality for lubricant base oil production, comprising:
   determining a wax content of a distillate feedstock fraction by differential scanning calorimetry;
   measuring at least two of a characteristic boiling point, a characteristic viscosity, and a refractive index for the distillate feedstock fraction;
   calculating a distillate dewaxed viscosity index (DDVI) at −9° C. for the distillate feedstock fraction based on the determined wax content and the measured at least two of the characteristic boiling point, the characteristic viscosity, and the refractive index, the calculated DDVI being at least 0 at −9° C.; and
   processing the feedstock to form a lubricant base oil having a viscosity index of at least 80 and a pour point of 0° C. or less.

16. The method of claim 15, wherein the wax content of the distillate feedstock fraction is determined based on the relationship $W = \Delta H / A(T)$, where W is the wax content, $\Delta H$ is a heat of fusion, T is a temperature where a freezing transition occurs, and A(T) is a scaling factor.

* * * * *